US009945672B2

(12) United States Patent
Balasubramanian et al.

(10) Patent No.: US 9,945,672 B2
(45) Date of Patent: Apr. 17, 2018

(54) WEARABLE DEVICE FOR TRACKING REAL-TIME AMBIENT HEALTH CONDITIONS AND METHOD FOR DESTINATION SELECTION BASED ON TRACKED REAL-TIME AMBIENT HEALTH CONDITIONS

(71) Applicant: INTERNATIONAL BUSINESS MACHINES CORPORATION, Armonk, NY (US)

(72) Inventors: Swaminathan Balasubramanian, Southfield, MI (US); Thomas G. Lawless, III, Poughkeepsie, NY (US); Jason Richard Malinowski, Southbury, CT (US); Cheranellore Vasudevan, Austin, TX (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 0 days.

(21) Appl. No.: 15/175,720

(22) Filed: Jun. 7, 2016

(65) Prior Publication Data

US 2017/0350702 A1    Dec. 7, 2017

(51) Int. Cl.
| | |
|---|---|
| *G01C 21/00* | (2006.01) |
| *H04W 4/00* | (2009.01) |
| *G01S 19/42* | (2010.01) |
| *G01S 5/02* | (2010.01) |
| *A61B 5/00* | (2006.01) |

(Continued)

(52) U.S. Cl.
CPC ............... *G01C 21/00* (2013.01); *A61B 5/01* (2013.01); *A61B 5/02438* (2013.01); *A61B 5/14532* (2013.01); *A61B 5/681* (2013.01); *G01S 5/0294* (2013.01); *G01S 19/42* (2013.01); *H04W 4/008* (2013.01); *H04W 4/025* (2013.01)

(58) Field of Classification Search
CPC ....... G01C 21/00; A61B 5/01; A61B 5/02438; A61B 5/14532; A61B 5/681; G01S 19/42; H04W 4/008; H04W 4/025
See application file for complete search history.

(56) References Cited

U.S. PATENT DOCUMENTS

| | | | |
|---|---|---|---|
| 2005/0015197 A1* | 1/2005 | Ohtsuji | G01C 21/34 701/533 |
| 2008/0246629 A1 | 10/2008 | Tsui et al. | |

(Continued)

*Primary Examiner* — Aaron L Troost
(74) *Attorney, Agent, or Firm* — F. Chau & Associates, LLC

(57) ABSTRACT

A system for providing destination guidance based on tracked real-time ambient health conditions includes one or more location tracking devices carried by one or more participants. The one or more location tracking devices track the locations of the one or more participants and providing the tracked locations to a central server when it is determined that the one or more participants are infected by a communicable ailment. The central server receives the provided tracked locations and transmits the tracked locations to a navigation guidance device carried by a user, without transmitting identifying details about the one or more participants. The navigation guidance device carried by the user provides guidance to the user on selecting a destination or route that avoids contact with or exposure to the plurality of participants.

19 Claims, 4 Drawing Sheets

(51) Int. Cl.
  *A61B 5/02* (2006.01)
  *A61B 5/01* (2006.01)
  *A61B 5/145* (2006.01)
  *H04W 4/02* (2018.01)
  *A61B 5/024* (2006.01)

(56) References Cited

U.S. PATENT DOCUMENTS

| | | | |
|---|---|---|---|
| 2011/0172903 A1* | 7/2011 | Farr | G01C 21/3461 |
| | | | 701/533 |
| 2013/0189944 A1 | 7/2013 | McCoy | |
| 2015/0100330 A1* | 4/2015 | Shpits | G06F 19/3493 |
| | | | 705/2 |
| 2015/0170296 A1 | 6/2015 | Kautz et al. | |
| 2015/0318885 A1* | 11/2015 | Earle | H04B 1/385 |
| | | | 455/575.6 |
| 2016/0327401 A1* | 11/2016 | Stenneth | G01C 21/3461 |

\* cited by examiner

WEARABLE DEVICE FOR TRACKING REAL-TIME AMBIENT HEALTH CONDITIONS AND METHOD FOR DESTINATION SELECTION BASED ON TRACKED REAL-TIME AMBIENT HEALTH CONDITIONS

BACKGROUND

1. Technical Field

The present disclosure relates to tracking real-time ambient health conditions and, more specifically, to a wearable device for tracking real-time ambient health conditions and a method for destination selection based on tracked real-time ambient health conditions.

2. Discussion of Related Art

Wearable devices are computerized instruments that are worn by a user to perform various functions. Some of the most popular examples of wearable devices include fitness-tracking wearables that can perform functions such as tracking steps taken and routs traversed. Many wearable devices can also monitor the health condition of a user by tracking vital signs of the user such as heart beat.

Modern wearable devices may further be able to interface with healthcare and wellness professionals and institutions so that the health condition data monitored by wearable devices may be easily shared, and the data used to improve a level of care offered to the user.

Many modern wearable devices interface with a smartphone of the user and can work in tandem with the smartphone to enhance the functionality offered by the wearable device, and to enhance the function of smartphone features and applications. In particular, many users rely upon smartphone applications for navigation guidance. However, existing approaches for smartphone-implemented navigation guidance do not utilize health condition data that is tracked by wearable devices.

BRIEF SUMMARY

A system for providing destination guidance based on tracked real-time ambient health conditions includes one or more location tracking devices carried by one or more participants. The one or more location tracking devices track the locations of the one or more participants and providing the tracked locations to a central server when it is determined that the one or more participants are infected by a communicable ailment. The central server receives the provided tracked locations and transmits the tracked locations to a navigation guidance device carried by a user, without transmitting identifying details about the one or more participants. The navigation guidance device carried by the user provides guidance to the user on selecting a destination or route that avoids contact with or exposure to the plurality of participants.

The one or more location tracking devices may include a GPS receiver for determining coordinates of the one or more participants and a radio for communicating the determined coordinates to the central server. The GPS receiver and the radio may be part of a smartphone device. The GPS receiver and the radio may be part of a wearable device.

The navigation guidance device may be a satellite navigation system. The navigation guidance device may be a smartphone device. The one or more participants or another entity may specify when the one or more participants are infected by a communicable ailment or otherwise in danger of spreading the communicable ailment.

A wearable device may be worn by the one or more participants to automatically determine when the one or more participants are infected by a communicable ailment or otherwise in danger of spreading the communicable ailment.

A wearable device may be worn by the user to automatically determine when the user is susceptible to the communicable ailment.

A method for providing destination guidance based on tracked real-time ambient health conditions includes determining when a user initiates ambient health condition avoidance. The location of the user is tracked when it is determined that the user has initiated ambient health condition avoidance. A health condition of each of a plurality of participants is tracked. It is determined when at least one of the plurality of participants carries a communicable ailment based on the tracked health conditions. The location of the at least one participant is tracked when it is determined that the at least one participant carries a communicable ailment. Destination selection assistance or navigation guidance is provided to the user to assist the user in avoiding contact with or proximity to the at least one participant using the tracked location of the user and the at least one participant.

Determining when the user initiates ambient health condition avoidance may include receiving an instruction from the user to initiate ambient health condition avoidance.

Determining when the user initiates ambient health condition avoidance may include monitoring the user's health condition for susceptibility to the communicable ailment.

Tracking the health condition of each of the plurality of participants may include monitoring vital signs of each of the plurality of participants using a wearable device.

Tracking the health condition of each of the plurality of participants may include monitoring patient records of the plurality of participants using an electronic medical records system.

Tracking the health condition of each of the plurality of participants may include periodically querying each of the plurality of participants for health status.

Tracking the health condition of each of the plurality of participants may include waiting for a notification of health status from one of the plurality of participants.

Determining when at least one of the plurality of participants carries a communicable ailment may be performed based on the tracked health conditions includes cross-referencing the tracked health conditions with communicable ailments using a medical knowledgebase.

Providing destination selection assistance to the user may include receiving a destination type from the user, locating a plurality of candidate destinations of the received type, determining which of the plurality of candidate destinations are proximate to the tracked locations of the at least one participant, removing candidate destinations proximate to the tracked locations of the at least one participant from the plurality of candidate destinations, and presenting the remaining candidate destinations to the user for selection.

Providing navigation guidance to the user may include receiving a destination from the user, locating a plurality of candidate routes to the received destination, determining which of the plurality of candidate routes are proximate to the tracked locations of the at least one participant, removing candidate routes proximate to the tracked locations of the at least one participant from the plurality of candidate routes, presenting the remaining candidate routes to the user for selection, when there is at least one remaining candidate route, and notifying the user when there are no candidate routes that are not proximate to the tracked locations of the at least one participant.

A computer system includes a processor and a non-transitory, tangible, program storage medium, readable by the computer system, embodying a program of instructions executable by the processor to perform method steps for providing destination guidance based on tracked real-time ambient health conditions. The method comprises determining when a user initiates ambient health condition avoidance, tracing the location of the user when it is determined that the user has initiated ambient health condition avoidance, tracking a health condition of each of a plurality of participants, determining when at least one of the plurality of participants carries a communicable ailment based on the tracked health conditions, tracking the location of the at least one participant when it is determined that the at least one participant carries a communicable ailment, and providing destination selection assistance or navigation guidance to the user to assist the user in avoiding contact with or proximity to the at least one participant using the tracked location of the user and the at least one participant.

Providing destination selection assistance to the user may include receiving a destination type from the user, locating a plurality of candidate destinations of the received type, determining which of the plurality of candidate destinations are proximate to the tracked locations of the at least one participant, removing candidate destinations proximate to the tracked locations of the at least one participant from the plurality of candidate destinations, and presenting the remaining candidate destinations to the user for selection. Providing navigation guidance to the user may include receiving a destination from the user, locating a plurality of candidate routes to the received destination, determining which of the plurality of candidate routes are proximate to the tracked locations of the at least one participant, removing candidate routes proximate to the tracked locations of the at least one participant from the plurality of candidate routes, presenting the remaining candidate routes to the user for selection, when there is at least one remaining candidate route, and notifying the user when there are no candidate routes that are not proximate to the tracked locations of the at least one participant.

BRIEF DESCRIPTION OF THE SEVERAL VIEWS OF THE DRAWINGS

A more complete appreciation of the present disclosure and many of the attendant aspects thereof will be readily obtained as the same becomes better understood by reference to the following detailed description when considered in connection with the accompanying drawings, wherein.

DETAILED DESCRIPTION

Figure 1:
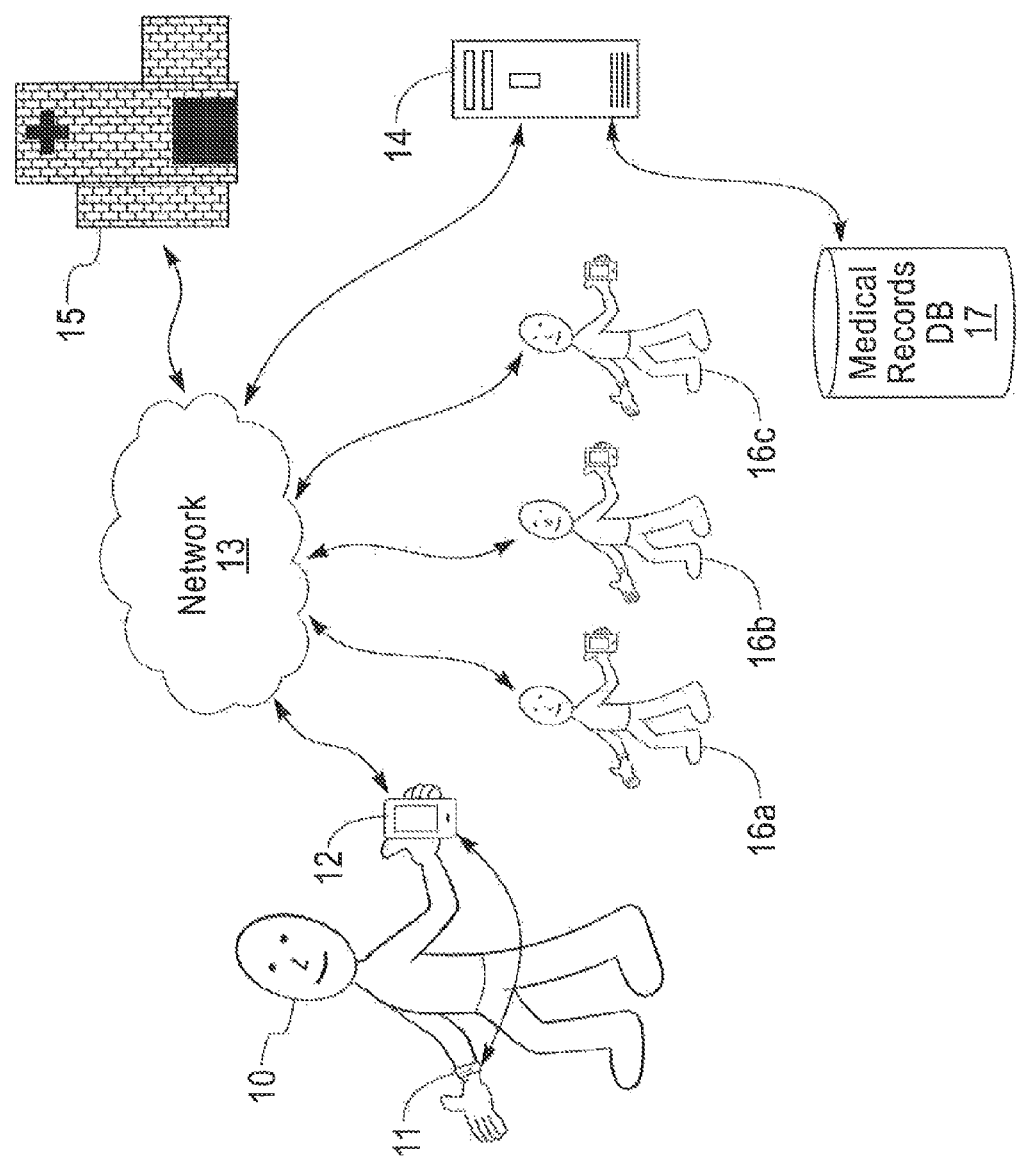
FIG. 1 is a schematic diagram illustrating an arrangement for tracking real-time ambient health conditions and providing destination/route guidance in accordance with exemplary embodiments of the present invention.

In describing exemplary embodiments of the present disclosure illustrated in the drawings, specific terminology is employed for sake of clarity. However, the present disclosure is not intended to be limited to the specific terminology so selected, and it is to be understood that each specific element includes all technical equivalents which operate in a similar manner.

Exemplary embodiments of the present invention may utilize wearable devices, smartphones, and/or medical records data to monitor the health condition of a set of participants. Similarly, wearable devices, smartphones, and/or medical records data may be used to monitor the health condition of a user. The user may be one of the participants, however, for the purpose of providing a simplified description, the user is distinguished from the other participants. It is to be understood that any participant may, at times, be the user, for reasons described below.

Exemplary embodiments of the present invention use the monitored health condition information to identify a person with a medical susceptibility and one or more people with an ailment that the person with the medical susceptibility may be particularly vulnerable to. The person with the identified medical susceptibility is referred to herein as "the user" while the people with the ailments are referred to as "the participants."

For example, the user may be an immunocompromised patient and the participants may be patients carrying a communicable disease that may threaten the health of the immunocompromised patient. The user may alternatively be a pregnant woman, a newborn baby, or an elderly patient and the participants may be patients carrying a communicable disease that is particularly dangerous to a pregnant woman, a newborn baby, or an elderly patient. Alternatively, the user may be a patient with a severe food allergy and the participants may be people carrying or consuming the allergen food.

When such a match has been made between a user and one or more participants, exemplary embodiments of the present invention may use the location and route data, acquired by the wearable device and/or the smartphones, to track the location and route of the user and participants.

As described herein, location may indicate the global coordinates of the person in question and route data may include a set of past locations with respect to time (e.g. the path recently taken by the person) as well as a predicted future course of movement, which is derived from the person's trajectory, past movements, and/or, where the person is in the process of using navigation assistance, for example, implemented on the person's smartphone, the programmed destination and selected route.

By examining the location and routes of the user as well as the participants, exemplary embodiments of the present invention may be used to issue avoidance alerts to the user and may also interface directly with the user's smartphone-implemented navigation guidance in such a way as to help the user to select alternative routes and/or alternative destinations so as to avoid crossing paths with the participants within some period of time ("time buffer") that is calculated according to the nature of the communicability of the disease (e.g. whether the disease is airborne, spread by fluid, or spread by direct contact) and how long the given disease is able to maintain communicability. For example, a disease that is spread only by direct contact may lead to a relatively small time buffer, which is to say, the user may be warned/guided to prevent them being at the same place at the same time, while for a disease that is spread by fluids, there may be a relatively long buffer time, which is to say, the user may be warned/guided to prevent them from being at a place that the participant has been in some number of minutes, hours, or days ago.

As mentioned above, destination selection is one way in which exemplary embodiments of the present invention may help the user avoid crossing paths with the participants. According to this approach, the user would use a smartphone to find a destination, for example, a coffee shop, and the user may be presented with a selection of destinations that matched participants are not at, have not been to, and/or are not on their way to.

In this way, exemplary embodiments of the present invention may be used to augment smartphone-implemented navigation guidance by taking into account health condition data that is tracked by wearable devices utilized by a group of participants whose location and route is tracked. The health and safety of the user may therefore be protected.

FIG. 1 is a schematic diagram illustrating an arrangement for tracking real-time ambient health conditions and providing destination/route guidance in accordance with exemplary embodiments of the present invention. A user 10 may carry a wearable device 11 such as a fitness tracker or smartwatch. An example of a fitness tracker is FITBIT sold by FITBIT INC. and an example of a smartwatch is APPLE WATCH sold by APPLE INC., however, other products are commercially available.

The wearable device 11 may include one or more health and movement sensors for monitoring the health condition of the user 10. Examples of health sensors include hear rate monitor, blood glucose sensor, thermocouple etc. and examples of movement sensors include an accelerometer, etc.

The user may also carry a smartphone 12, which may receive data from the wearable device 11, for example, wirelessly using communications standards such as Bluetooth low energy (BTLE), designed and marketed by the BLUETOOTH SPECIAL INTEREST GROUP.

The smartphone 12 may be configured for providing navigation guidance as well as health and location monitoring as described herein. The smartphone 12 may be equipped with a touch-sensitive display for handling I/O, a BLUETOOTH radio for communicating with the wearable device 11, a GPS radio for aiding in navigation guidance, and a CPU for performing the processing functions described herein.

The smartphone 12 may be in communication with a central server 14 over a wide-area computer network 13 such as the Internet. The smartphone 12 may include a cellular radio for maintaining this connection. The cellular radio may be, for example, an LTE radio, however, other forms of cellular radio may be included.

The smartphone 12 may have one or more application and core functions installed thereon for the performance of the steps described below, for interacting with the central server 14, and for providing navigation guidance.

The central server 14 may be embodied as a single physical host machine, a cluster of host machines, a distributed set of host machines, one or more virtual machines running on one or more physical hosts, or as some other computational construct. The central server 14 may also be in communication with a medical records database 17 that stores medical records for the user and a group of participants 16a, 16b, 16c, for example, over the network 13. The central server 14 may also be in communication with a healthcare institution 15 such as a clinic, hospital, research facility, etc.

The group of participants 16a, 16b, 16c may similarly be outfitted with wearable devices and smartphones.

Figure 2:
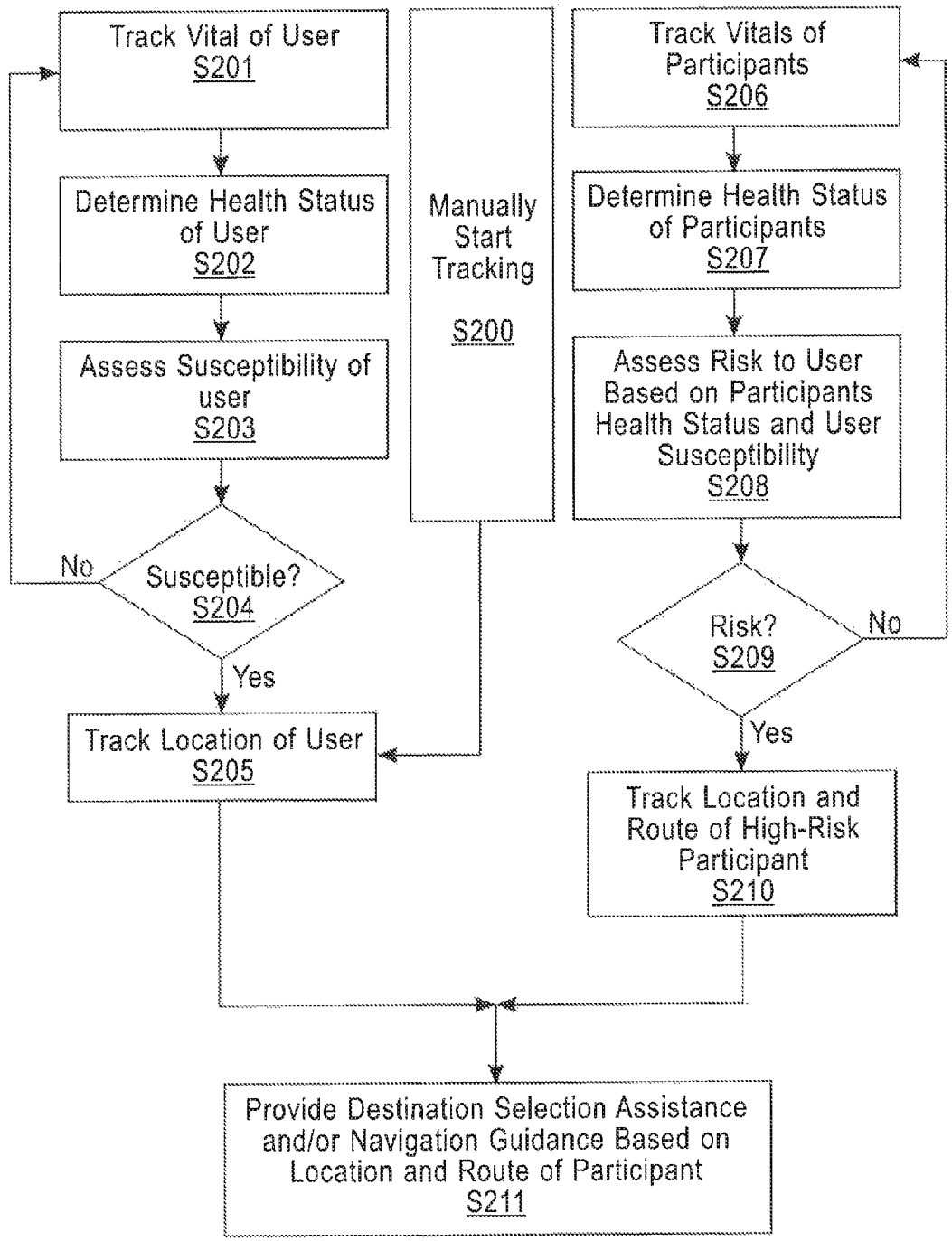
FIG. 2 is a flow chart illustrating an approach for tracking real-time ambient health conditions and providing destination/route guidance in accordance with exemplary embodiments of the present invention.

FIG. 2 is a flow chart illustrating an approach for tracking real-time ambient health conditions and providing destination/route guidance in accordance with exemplary embodiments of the present invention. As described above, health data such as vital signs, may be tracked for the user 10, for example, using the user's wearable device 11 (Step S201). Based on this tracked health data, medical records for the user retrieved from the medical records database 17, and/or user input, a health status of the user may be determined (Step S202). In this context, health status is defined as information pertaining to whether the user 10 is particularly susceptible to one or more diseases. If the user is determined not to be susceptible (No, Step S204), then the process may end or the steps S201-S203 may be periodically repeated unless and until the user is determined to be susceptible (Yes, Step 204).

When it is determined that the user is susceptible (Yes, Step S204), the location and route of the user is tracked, for example, using the wearable device 11 and/or the smartphone 12 (Step S205).

According to some exemplary embodiments of the present invention, there need not be any estimation as to whether the user is susceptible to a particular disease condition. Exemplary embodiments of the present invention may be used, for example, by parents wishing to protect their children, or by caregivers wishing to protect the elderly from diseases, generally. Accordingly, steps S201-S204 may be optionally omitted in such a use case. Rather, the user may simply select tracking to begin (Step S200).

Meanwhile, health data such as vital signs, may be tracked for the participants 16(a,b,c), for example, using the participants' wearable devices (Step S206). Based on this tracked health data, medical records for the participants retrieved from the medical records database 17, and/or participant input, health status of the participants may be determined (Step S207). The health status of each participant is used to determine whether that participant represents a risk to the user (Step S208). If a given participant is determined not to be a risk (No, Step S209), then the process may end or the steps S206-S208 may be periodically repeated unless and until the participant is determined to be a risk (Yes, Step S209). In this context, the participant may be considered to be a risk if the user has a communicable ailment that is likely to be transmitted by proximity or general contact, such as diseases that are spread by air or surface contact. Thus the determination as to whether the participant is a risk to the user need not consider actual susceptibilities of the user.

If one or more participants are determined to be a risk to the user (Yes, Step S209), then the location/route of those participants will be tracked (Step S210).

It is to be noted that steps S201-S205 are, in many ways, similar to Steps S206-S210. According to exemplary embodiments of the present invention, the users and participants need not be differentiated up until this point, and in assessing the susceptibility of the user (Step S203) a user may be identified from among the participants. There may even be multiple users, in which case the participants risk to users will be separately determined with respect to each identified user at Step S208.

Thereafter, destination selection and/or navigation guidance may be provided to the user in such a way as to avoid the crossing of paths between the user and the high-risk participants within the calculated time buffer, as described above (Step S211).

Figure 3:
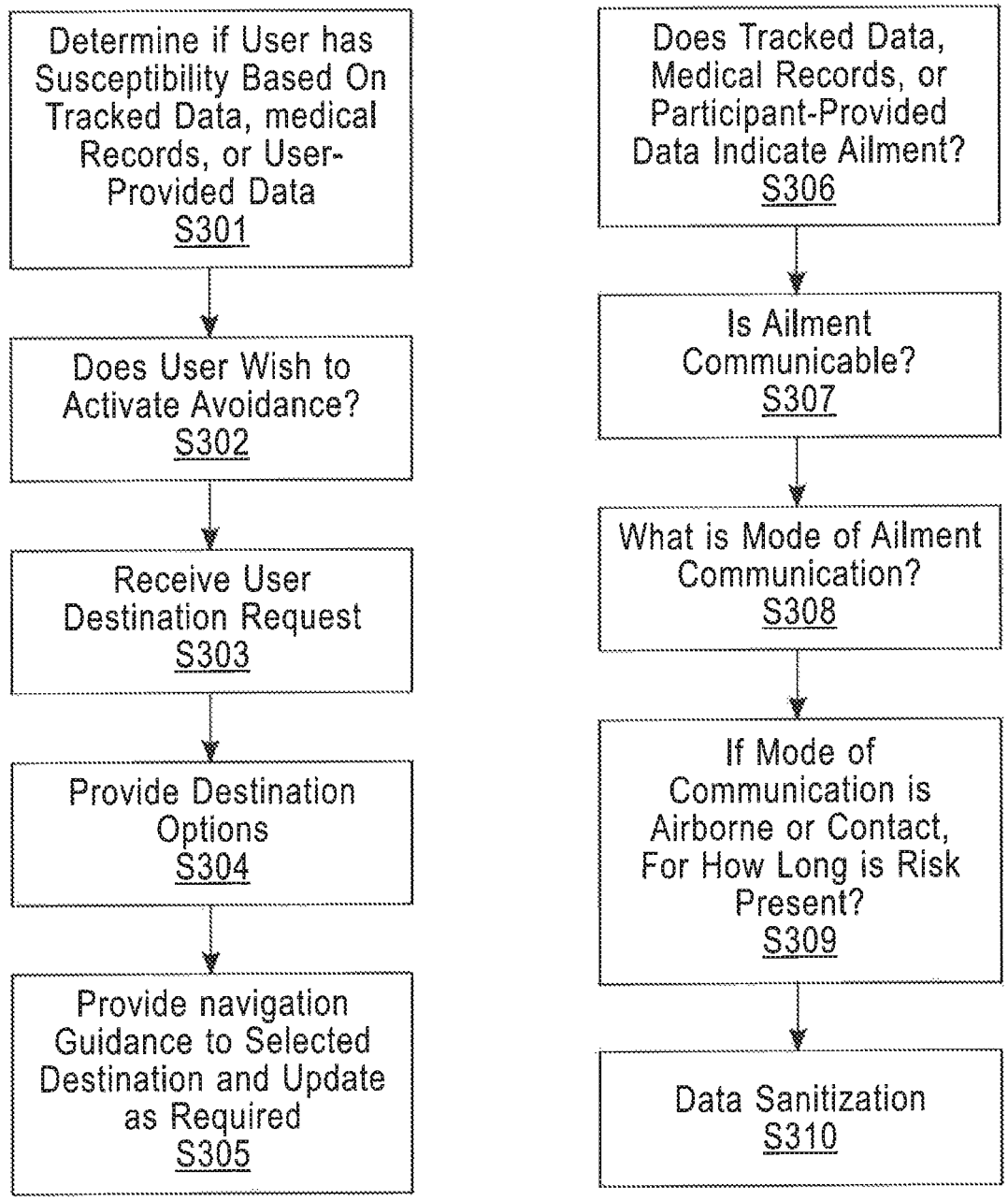
FIG. 3 is a flow chart illustrating a detailed view of these steps in accordance with an exemplary embodiment of the present invention.

As discussed above, in tracking real-time ambient health conditions according to exemplary embodiments of the present invention, the susceptibility of the user is assessed (Step S203) and the risk posed to the user by the health condition of the participants is assessed (Step S208). FIG. 3 is a flow chart illustrating a detailed view of these steps in accordance with an exemplary embodiment of the present invention.

In assessing the susceptibility of the user, it may be determined whether the tracked fitness/health data, the medical records, and/or user-provided data are indicative of an ailment or condition that would (Step S301). In one simple example, the medial records may explicitly provide that the user has such a condition, or in another simple example, the user may identify him or herself as having such a condition, for example, by an input made to an application installed on the user's smartphone.

According to more complex examples, the tracked fitness/health data may be suggestive of such an ailment or condition and the user and/or the user's health care provider/institution 15 may be queried to confirm or reject the suggestion.

This determination may be made locally by the application running on the user's smartphone 12, or remotely via the network 13, for example, by the central server 14.

Where the user has been determined to be susceptible, the user may be prompted to indicate whether he or she wishes to activate the avoidance feature of the smartphone application, or the user may independently invoke the avoidance feature (Step S302). By invoking the avoidance feature, the user is expressing a willingness to have ambient health conditions tracked and/or to have destination selection aided in accordance with ambient health conditions.

Where the user invokes ambient health conditions tracking, an area map may be displayed with locations and routes of high-risk participants highlighted. Where the user invokes destination selection, the user may be prompted to provide a destination request, for example, to input where or what sort of establishment the user wishes to travel to. After the user destination request is received (Step S303), a set of destination options may be provided to the user (Step S304). For example, where the destination request is a coffee house, a set of nearby coffee houses may be displayed, with those coffee houses that coincide with the location or route of high-risk participants being first removed. According to some exemplary embodiments of the present invention, the user may be prevented from receiving a display with locations and routes of high-risk participants highlighted thereon, and instead, the user might be restricted to destination options. In this way, the exact location of the high-risk participants may be made inaccessible to the user, and so the participants may feel a greater willingness to participate in the system knowing that their location and route cannot be directly observed by others.

The initial list of possible destinations and their corresponding locations may be collected from available mapping services such as GOOGLE MAPS, provided by Google. Inc., for example, by interfacing with a suitable API.

Thereafter, the user may select from among the list of the restricted destination options and navigation guidance may be provided (Step S305), for example, again using an available mapping service. It may happen that none of the possible destination locations represent an ambient health risk, and in such a case, all destination candidates may be provided to the user. According to an exemplary embodiment of the present invention, the user might not be able to determine for sure whether one or more possible destination locations have been removed.

In assessing the risk posed by a given participant to the user, first it may be determined if the participants has an ailment that could be a risk to the user. This may be performed, for example, using the tracked health/activity data, medical records, and/or participant-provided data (Step S306). This step is similar in many ways to step S301 discussed above. In making this determination, patient medical records or an encyclopedia of medical knowledge may be referenced. Thus, the present approach may be able to make use of a medical knowledgebase without the need for records of a specific user (e.g. patent), however, where such individualized records are available, they may be used. The encyclopedia of medical knowledge may be embodied, for example, as a table defining which ailments represent a high risk to which patient-susceptibilities.

The encyclopedia of medical knowledge may determine not only if the ailment of the participant is a risk to the user, but also, whether the ailment is communicable, and if so, how it is transmitted (Step S308). For example, possible vectors of transmission may include airborne transmission, contact transmission, or fluid transmission, and may further be used to determine how long a location represents a risk to the user, after the participant has left a given location, as some pathogens have a better ability to survive in the air and on surfaces than other pathogens.

The results of these determinations may be stripped of all identifying data so the identity of the individual participants is not revealed (Step S310). For example, as discussed above, the user might only see that some locations or destination options are highlighted as risky for as long as it is calculated that the risk of exposure and/or transmission lingers, and the user might not be able to see who the participants are, where the participants are, or what ailments they have.

The user and participants may interact with the above-described system using a mobile application installed on their respective smart phones. The mobile applications may pass interactions to the central server, which may be responsible for performing the above-described analysis. However, where available computational power is present in the aforementioned smartphones, some processing may be performed locally, with the exception that personal information concerning the participants is never passed to the user's smartphone for processing.

Figure 4:
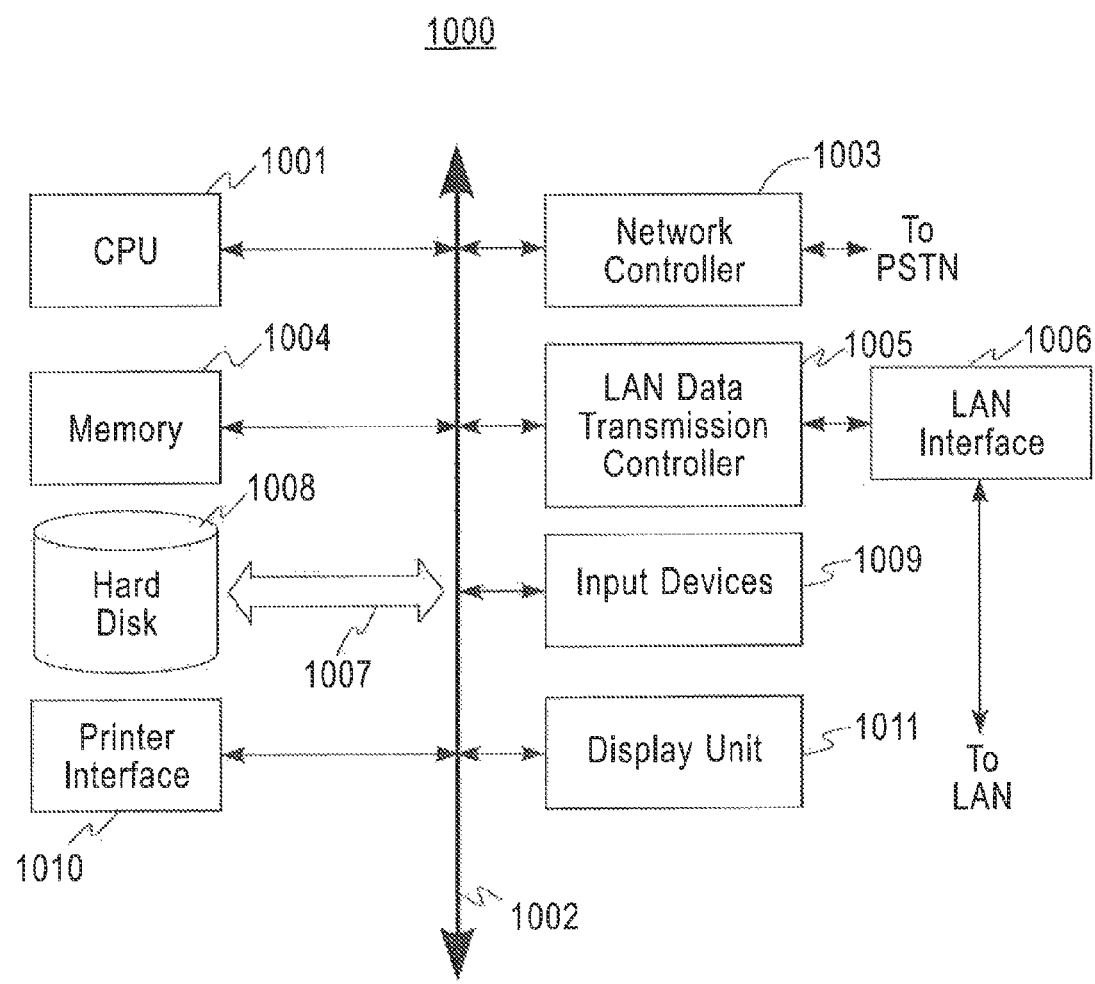
FIG. 4 shows an example of a computer system capable of implementing the method and apparatus according to embodiments of the present disclosure.

FIG. 4 shows an example of a computer system which may implement a method and system of the present disclosure. The system and method of the present disclosure may be implemented in the form of a software application running on a computer system, for example, a mainframe, personal computer (PC), handheld computer, server, etc. The software application may be stored on a recording media locally accessible by the computer system and accessible via a hard wired or wireless connection to a network, for example, a local area network, or the Internet.

The computer system referred to generally as system 1000 may include, for example, a central processing unit (CPU) 1001, random access memory (RAM) 1004, a printer interface 1010, a display unit 1011, a local area network (LAN) data transmission controller 1005, a LAN interface 1006, a network controller 1003, an internal bus 1002, and one or more input devices 1009, for example, a keyboard, mouse etc. As shown, the system 1000 may be connected to a data storage device, for example, a hard disk, 1008 via a link 1007.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described herein with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowcharts and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

Exemplary embodiments described herein are illustrative, and many variations can be introduced without departing from the spirit of the disclosure or from the scope of the appended claims. For example, elements and/or features of different exemplary embodiments may be combined with each other and/or substituted for each other within the scope of this disclosure and appended claims.

What is claimed is:

1. A system for providing destination guidance based on tracked real-time ambient health conditions, comprising;
   one or more location tracking devices carried by one or more participants, the one or more location tracking devices tracking the locations of the one or more participants and providing the tracked locations to a central server when it is determined that the one or more participants are infected by a communicable ailment;
   the central server, receiving the provided tracked locations transmitting the tracked locations to a navigation guidance device carried by a user, without transmitting identifying details about the one or more participants;
   a wearable device worn by the user to monitor the user's health condition and automatically determine when the user is susceptible to the communicable ailment based on the user's monitored health condition; and
   the navigation guidance device carried by the user and providing guidance to the user on selecting a destination or route that avoids contact with or exposure to the plurality of participants when it is determined that the user is susceptible to the communicable ailment based on the user's monitored health condition.

2. The system of claim 1, wherein the one or more location tracking devices comprise a GPS receiver for determining coordinates of the one or more participants and a radio for communicating the determined coordinates to the central server.

3. The system of claim 2, wherein the GPS receiver and the radio are part of a smartphone device.

4. The system of claim 2, wherein the GPS receiver and the radio are part of a wearable device.

5. The system of claim 1, wherein the navigation guidance device is a satellite navigation system.

6. The system of claim 1, wherein the navigation guidance device is a smartphone device.

7. The system of claim 1, wherein the one or more participants or another entity specifies when the one or more participants are infected by a communicable ailment or otherwise in danger of spreading the communicable ailment.

8. The system of claim 1, additionally comprising a wearable device worn by the one or more participants to automatically determine when the one or more participants are infected by a communicable ailment or otherwise in danger of spreading the communicable ailment.

9. A method for providing destination guidance based on tracked real-time ambient health conditions, comprising;
   determining when a user initiates ambient health condition avoidance;
   tracing the location of the user when it is determined that the user has initiated ambient health condition avoidance;
   monitoring the user's health condition;
   tracking a health condition of each of a plurality of participants;
   determining when at least one of the plurality of participants carries a communicable ailment based on the tracked health conditions;
   automatically determining when the user is susceptible to the communicable ailment based on the user's monitored, health condition;
   tracking the location of the at least one participant when it is determined that the at least one participant carries a communicable ailment; and
   providing destination selection assistance or navigation guidance to the user to assist the user in avoiding contact with or proximity to the at least one participant using the tracked location of the user and the at least one participant when it is determined that the user is susceptible to the communicable ailment based on the user's monitored health condition.

10. The method of claim 9, wherein determining when the user initiates ambient health condition avoidance includes receiving an instruction from the user to initiate ambient health condition avoidance.

11. The method of claim 9, wherein tracking the health condition of each of the plurality of participants includes monitoring vital signs of each of the plurality of participants using a wearable device.

12. The method of claim 9, wherein tracking the health condition of each of the plurality of participants includes monitoring patient records of the plurality of participants using an electronic medical records system.

13. The method of claim 9, wherein tracking the health condition of each of the plurality of participants includes periodically querying each of the plurality of participants for health status.

14. The method of claim 9, wherein tracking the health condition of each of the plurality of participants includes waiting for a notification of health status from one of the plurality of participants.

15. The method of claim 9, wherein determining when at least one of the plurality of participants carries a communicable ailment based on the tracked health conditions includes cross-referencing the tracked health conditions with communicable ailments using a medical knowledgebase.

16. The method of claim 9, wherein providing destination selection assistance to the user includes:
   receiving a destination type from the user;
   locating a plurality of candidate destinations of the received type;
   determining which of the plurality of candidate destinations are proximate to the tracked locations of the at least one participant;
   removing candidate destinations proximate to the tracked locations of the at least one participant from the plurality of candidate destinations; and
   presenting the remaining candidate destinations to the user for selection.

17. The method of claim 9, wherein providing navigation guidance to the user includes:
   receiving a destination from the user;
   locating a plurality of candidate routes to the received destination;
   determining which of the plurality of candidate routes are proximate to the tracked locations of the at least one participant;
   removing candidate routes proximate to the tracked locations of the at least one participant from the plurality of candidate routes;
   presenting the remaining candidate routes to the user for selection, when there is at least one remaining candidate route; and
   notifying the user when there are no candidate routes that are not proximate to the tracked locations of the at least one participant.

18. A computer system comprising:
   a processor; and
   a non-transitory, tangible, program storage medium, readable by the computer system, embodying a program of instructions executable by the processor to perform method steps for providing destination guidance based on tracked real-time ambient health conditions, the method comprising:

determining when a user initiates ambient health condition avoidance;

tracing the location of the user when it is determined that the user has initiated ambient health condition avoidance;

monitoring the user's health condition;

tracking a health condition of each of a plurality of participants;

determining when at least one of the plurality of participants carries a communicable ailment based on the tracked health conditions;

automatically determining when the user is susceptible to the communicable ailment based on the user's monitored health condition;

tracking the location of the at least one participant when it is determined that the at least one participant carries a communicable ailment; and providing destination selection assistance or navigation guidance to the user to assist the user in avoiding contact with or proximity to the at least one participant using the tracked location of the user and the at least one participant when it is determined that the user is susceptible to the communicable ailment based on the user's monitored health condition.

19. The computer system of claim 18, wherein:

providing destination selection assistance to the user includes:

receiving a destination type from the user;

locating a plurality of candidate destinations of the received type;

determining which of the plurality of candidate destinations are proximate to the tracked locations of the at least one participant;

removing candidate destinations proximate to the tracked locations of the at least one participant from the plurality of candidate destinations; and presenting the remaining candidate destinations to the user for selection, and providing navigation guidance to the user includes:

receiving a destination from the user;

locating a plurality of candidate routes to the received destination;

determining which of the plurality of candidate routes are proximate to the tracked locations of the at least one participant;

removing candidate routes proximate to the tracked locations of the at least one participant from the plurality of candidate routes;

presenting the remaining candidate routes to the user for selection, when there is at least one remaining candidate route; and notifying the user when there are no candidate routes that are not proximate to the tracked locations of the at least one participant.

* * * * *